United States Patent
Killoren Clark et al.

(10) Patent No.: US 7,912,674 B2
(45) Date of Patent: Mar. 22, 2011

(54) METHOD FOR PROCESSING A CHRONOLOGICAL SEQUENCE OF MEASUREMENTS OF A TIME DEPENDENT PARAMETER

(75) Inventors: Amy Killoren Clark, Montprevereyes (CH); Kelly Heaton, Lugano (CH)

(73) Assignee: Roche Diagnostics International AG, Steinhausen (CH)

( * ) Notice: Subject to any disclaimer, the term of this patent is extended or adjusted under 35 U.S.C. 154(b) by 0 days.

(21) Appl. No.: 12/431,904

(22) Filed: Apr. 29, 2009

(65) Prior Publication Data

US 2009/0271729 A1   Oct. 29, 2009

Related U.S. Application Data

(63) Continuation of application No. PCT/CH2007/000531, filed on Oct. 26, 2007.

(30) Foreign Application Priority Data

Oct. 31, 2006   (EP) ..................... 06405457

(51) Int. Cl.
*G06F 19/00* (2006.01)
(52) U.S. Cl. ...................................... 702/178
(58) Field of Classification Search ............ 702/178, 702/182–185
See application file for complete search history.

(56) References Cited

U.S. PATENT DOCUMENTS

| | | | |
|---|---|---|---|
| 7,052,472 B1 | 5/2006 | Miller et al. | |
| 2002/0002326 A1 | 1/2002 | Causey et al. | |
| 2003/0125612 A1 | 7/2003 | Fox et al. | |
| 2005/0004439 A1 | 1/2005 | Shin et al. | |
| 2005/0182358 A1* | 8/2005 | Veit et al. | 604/93.01 |
| 2006/0031094 A1 | 2/2006 | Cohen et al. | |

FOREIGN PATENT DOCUMENTS

| | | |
|---|---|---|
| EP | 0680727 A1 | 11/1995 |
| WO | 0019887 A1 | 4/2000 |

OTHER PUBLICATIONS

International Search Report dated Jan. 16, 2008.

* cited by examiner

*Primary Examiner* — Edward Raymond
(74) *Attorney, Agent, or Firm* — Dinsmore & Shohl LLP

(57) ABSTRACT

A method for processing a chronological sequence of measurements of a time dependent parameter measured in or on a human body, in particular of a physiological glucose concentration, and a system thereof are disclosed. A database stores a plurality of chronological sequences of measurements of the time dependent parameter and computing and display equipment graphically displays on a user interface display at least three of the measurements of a stored sequence simultaneously. The method as well as the system enable a patient to improve self-management skills concerning a therapy that affects the behavior of the parameter.

24 Claims, 9 Drawing Sheets

METHOD FOR PROCESSING A CHRONOLOGICAL SEQUENCE OF MEASUREMENTS OF A TIME DEPENDENT PARAMETER

CROSS REFERENCE TO RELATED APPLICATIONS

This application is a continuation of PCT Application PCT/CH2007/000531, filed 26 Oct. 2007, which claims priority to EP application Ser. No. 06405457.0, filed Oct. 31, 2006.

TECHNICAL FIELD

Embodiments of the invention relate to a method and a system for processing a chronological sequence of measurements of a time dependent parameter measured in or on a human body, in particular of a physiological glucose concentration. Embodiments of the invention further relate to a computer program for implementing the method for processing the chronological sequence of measurements of the time dependent parameter.

BACKGROUND ART

Monitoring parameters measured in or on the body of humans such as a concentration of a certain substance in a given body fluid has many applications. In particular, the monitoring is crucial in the context of therapies that involve an administration of active substances regulated depending on the value of one or a plurality of physiological parameters. A prominent example is diabetes therapy where the administration of insulin is effected depending on a measured glucose concentration in a body fluid of the patient.

Conventionally, diabetic patients who need to regularly administer insulin have periodically taken measurements of their blood glucose level, e.g. using a hand held strip-based glucose meter. However, the small number of measurements (usually four a day) provide only a very coarse picture of the progression of the glucose level ("snapshots" in time). They cannot give dynamic information about the metabolic response to a specific event such as a meal or physical activities of the patient; or more generally, the glucose trend during a period of time.

Continuous glucose monitoring (CGM) is a new technology for diabetes self-management. Instruments for continuous glucose monitoring record glucose concentrations over a period of time that lasts from several hours to several days, weeks or even months. The measurement frequency is much higher than that of the traditional spot blood glucose (bG) measurements referred to above (usually at least 10 measurements per hour). In principle, the increased temporal resolution provides the patient as well as his or her health care provider(s) (HCP) with a rich data set of time-variant glucose information. In principle, the continually measured glucose data can be used to more specifically adjust and refine the diabetes therapy to individual needs by adjusting the basal insulin rate as well as the timing and the amount of boluses. Furthermore, the data provides indications about advisable changes of the patient's behavior, e.g. concerning different food choices (type, portion) or activity changes.

However, there are several reasons why people with diabetes struggle to gain maximal benefit from Continuous Glucose Monitoring. First, a raw glucose signal over time can be complicated to understand. Continuous glucose monitoring is a data-intensive diagnostic tool and can therefore cause the user to become overwhelmed by an overload of information for which they have no use or explanation.

It is known to provide the user of CGM equipment with simplified real-time features such as trend arrows and hypo alarms. However, these features fail to give patients the "big picture" needed for deeper learning and behavior modification.

US 2005/004439 A1 (Medtronic MiniMed) relates to glucose monitoring systems and in particular to calibration methods for such systems. The calibration process involves obtaining glucose monitor data at predetermined intervals over a period of time as well as obtaining at least two reference glucose values from a reference source (e.g. a blood glucose meter) that correspond with the obtained glucose monitor data; starting from the corresponding data, calibration characteristics are calculated, which are subsequently used for calibrating the obtained glucose monitor data. The received data, i.e. the blood glucose history, may be analyzed, displayed and logged. A software is used to download the data, create a data file, calibrate the data, and display the data in various formats including charts, forms, reports, graphs, tables, lists, and the like. The displayed information includes trending information of the characteristic (e.g., rate of change of glucose), graphs of historical data, average characteristic levels (e.g., glucose), stabilization and calibration information, raw data, tables (showing raw data correlated with the date, time, sample number, corresponding blood glucose level, alarm messages, and more), and the like.

US 2003/125612 A1 (J. Kelly Fox et al.) relates to medical monitoring systems, in particular to blood glucose monitoring of diabetic people. The described system allows for performing predictive analyses to anticipate harmful conditions, such as hyperglycemic incidents. This process may involve repeatedly measuring the respective physiological value to obtain a series of physiological characteristic values to determine how the physiological characteristic is changing over time. Furthermore, the process may involve the extrapolation of curves, the calculation of averages of the series of physiological characteristic values or the calculation of line fits, e.g. over a defined span of time (e.g. one hour). The described systems aim at providing meaningful retrospective information to the patient using the sensor and at conveniently and efficiently storing and displaying such useful information. For this purpose the collected data may retrospectively be displayed in the form of a minimum and maximum data presentation, as an excursion data presentation, as a characteristic value distribution data presentation or as an integrated characteristic value data presentation.

WO 00/19887 A1 (Minimed) relates to telemetered subcutaneous sensor devices featuring wireless communication between an implantable subcutaneous sensor set, e.g. for measuring blood glucose, and a remotely located monitor. The monitor displays and logs the received glucose readings. The information displayed on the display of the monitor may include trending information of the characteristic (e.g., rate of change of glucose), graphs of historical data, average characteristic levels (e.g., glucose), or the like.

US 2002/002326 A1 (Minimed) relates to remote programs and/or handheld personal assistants (PDAs) for use with medical devices. The information displayed on the display of the monitor may include trending information of the characteristic (e.g., rate of change of glucose), graphs of historical data, average characteristic levels (e.g., glucose), or the like. Depending on the actual embodiment, the raw received sensor signals or calibrated or adjusted results may be stored for downloading, later analysis or review. US 2006/031094 A1 (Medtronic MiniMed) relates to systems and processes for managing data relating to medical or biological conditions of a plurality of subjects (e.g. diabetic subjects) over a wide area network. A corresponding system is realized by a group of software modules running on one or more servers connected to the wide-area network; the users may communicate with the medical data management system over the internet, whereas subject support devices (such as e.g. meters or biological sensors) may be connected to user-side computers. A subject support device, such as an infusion pump, may communicate with a plurality of meters or sensors (e.g. by wireless interfaces) and store information received from these further devices for later communication over the wide area network. Further information may be provided manually by the user by entering into the subject-side computer or the subject support device, e.g. information relating to a subject's activity, such as dietary information, eating times and amounts, exercise times and amounts, or the like. The system features a database layer that may include a centralized database repository that is responsible for warehousing and archiving stored data in an organized format for later access, and retrieval. The centrally stored data may be employed to analyze historical information regarding a subject's biological condition, operation of the subject support devices, treatment, personal habits, etc. A reporting layer may include a report wizard program that pulls data from selected locations in the database and generates report information from the desired parameters of interest. Reports may have the form of bar graphs, x-y coordinate graphs, pie charts, scatter charts, stacked bar charts, etc.

However, during retrospective analysis there is the common problem that the patient has already forgotten the specific circumstances that accompanied or caused a certain marked effect on the glucose level. In principle, maintaining a day-to-day log book is a solution to this problem, but requires considerable discipline.

Furthermore, if there is a multitude of different ways of displaying the (processed) information, many people are dependent on their HCP for interpreting the displayed data. Due to these reasons most people cannot fully benefit from CGM today because they must rely largely on HCPs for retrospective analysis and guidance on CGM data.

SUMMARY OF THE INVENTION

It is against the above background that embodiments of the invention enable a patient to improve self-management skills concerning his therapy and lifestyle choices.

In one embodiment, a time segment of the chronological sequence of measurements is stored as a record in a database and at least three of the measurements of the stored segment are simultaneously graphically displayed on a user interface display, such as a display of a PDA, a personal computer, a cellular or smart phone, a specific remote control for an infusion pump or of an analyte measuring device or combinations thereof.

Storing delimited segments of a theoretically everlasting sequence allows for identifying noteworthy events (e.g. the effects of a certain insulin administration and a certain meal onto the physiological glucose level) by corresponding graphical representations (shapes). Graphically displaying the segment, represented by a plurality of values of the parameter taken at different times, allows for intuitive pattern analysis of the measured data by the user or their HCP.

For most people it is much easier to remember or compare graphical pictures or shapes than numbers. Still, the human attention is overstrained by having to interpret or compare lengthy curves representing e.g. the progression of the measured parameter during a whole day or several days. Therefore, the option to see the graphically displayed data corresponding to a specific event helps the patient to remember previous events (that may be already stored in the database) with a similar pattern. Employing an intuitive graphic vocabulary gives non-professional users an improved and novel way to evaluate and use complex CGM data. Storing the sequence of measurements in the database allows for building up a personal archive of event-specific metabolic responses as sequences (or shapes) that can be accessed and cross-referenced.

It is important to note that the most important and challenging aspect of diabetes management is not controlling glucose levels during a fasting period. The real challenge is to control and/or compensate event-based glucose response, wherein an event is a meal, exercise or other metabolic challenge.

The measurements may be e.g. displayed in such a way that the values of the at least three measurements are displayed in a time-value coordinate system as time-value data pairs in relation to a reference line, i.e. values of the measurements (e.g. the glucose concentration) are displayed on a first axis of a graph, whereas time information on the measurements is displayed on a second axis of the graph.

Preferably, temporally adjacent data pairs are connected to build a curve and a geometrical area between the curve and the reference line is highlighted to build a characteristic shape corresponding to the stored time segment. Therefore, the corresponding areas above and below the reference line are read as "mountains" and "valleys" in function of the given reference line. The time scale as well as the value scale are preferably built in to the display area (bounding box) of the user interface display for easy recognition and differentiation. The described display mode allows for easily and rapidly reading multiple types of information from a single simple graphic space, namely: the duration of the displayed sequence of measurements (e.g. in 15-minute time intervals); the relative times spent with a value of the parameter above/below the baseline; the relative values of the parameter in comparison with a minimum as well as with a maximum (inferred from the baseline as well as from minimum/maximum indicators on the display); and the rates of change (slope).

The detailed information will improve the patient's self-management skills concerning his therapy. It will allow him or her to improve choosing the amount and timing for boluses and help adjusting the basal rate (in cooperation with the HCP) to an optimum level.

It is advantageous if a device is used for displaying the records and for operating the system that the user is already familiar with, such as a mobile/smart phone, a PDA or an MP3 player. This will substantially ease familiarization with the user interface.

The reference line preferably corresponds to a reference value of the parameter (such as a favorable target value or a threshold value). This allows for easy determination whether a given value, e.g. the current parameter value, is below or above this reference. A reference value could be fasting glucose, hypoglycemic threshold or hyperglycemic threshold. Shapes displayed in relation to a predetermined reference value may be easily compared by comparing "mountains" and "valleys" corresponding to time intervals in which the value is above or below the reference value ("sea level"), respectively.

It is preferred that the reference value is changeable by a user (the patient or its HCP). In the case of a change all data stored in the database is updated according to the changed reference value. Whereas the visual appearance of a shape (position and size of "valleys" and "mountains") strongly depends on the position of the reference line, the time-value data pairs itself are not affected by changing the reference value. This allows for a re-interpretation of previous records according to the new reference value such as e.g. to an optimum target value. Furthermore, comparability between earlier and later records is ensured.

In one embodiment, a method according to the present invention is particularly advantageous for diabetic patients, where the parameter is a glucose concentration measured by a continuous glucose measurement (CGM) system. CGM provides a high temporal resolution that allows for identifying long as well as mid and short term consequences of a certain event (a certain meal, an insulin bolus of a certain amount, physical activities, etc.) on the glucose level.

However, in principle the method is also applicable in connection with the monitoring of other time dependent parameters measured in or on the human body such as other substance concentrations (e.g. exogenous insulin), physiological characteristics like conductivity, physiological vital signs like heart or breath rate, temperature, movement, air- or structure-borne sound, ECG (electrocardiogram) etc.

The measurements of the glucose level may be performed in one embodiment by a continuous glucose sensor device which is placed in or on a human body in order to measure glucose values in interstitial fluid. The measurements are transmitted to a computing and display equipment, in particular to a PDA, a personal computer, a cellular or smart phone, a specific remote control for an infusion pump, an analyte measuring device such as a glucose measuring device such as e.g. a hand held glucose meter, more preferably a strip based glucose meter, or combinations thereof. The computing and display equipment stores the measured values in the database and graphically displays desired sequences on the user interface display which may be e.g. a liquid-crystal (LCD), LED or OLED display.

Preferably, the measurements are transmitted from the sensor device to the computing and display equipment by wireless communication, in particular by RF communication. Suitable standards such as "Bluetooth" and corresponding equipment exist and are easily available. Suitable data communication means are e.g. described in EP 1 688 085 A1 (Disetronic Licensing AG).

Alternatively, the measurements may be transmitted by wired links. For some applications it may be adequate to transmit the measurements by directly contacting the computing and display equipment by the sensor device. The transmission of the information may happen while the sensor device is placed on the human body and/or after the sensor device (such as a "patch" device) has been removed from the human body.

Advantageously, the computing and display equipment comprises means for receiving user input, in particular push-buttons or a touchscreen, and means for editing and/or managing sequences stored in the database, depending on the user input.

The functionality of the computing and display equipment may be fully or partly realized in hardware or firmware. However, preferentially it will be partly or fully provided by a computer program product that when run on the computing and display equipment will carry out the inventive method as described above and in the following. In principle, this allows for using commercially available devices as listed above for processing and displaying the measurements.

People have individual preferences for meaningful time and/or data intervals which raw CGM curves and standard timelines cannot address. Therefore, it is preferred that a temporal start point and end point corresponding to an event are defined, in particular that they are specified by the user, and that measurements of the sequence lying in between said start point and said end point are included in the record to be stored in the database. Allowing people to define their own time and data segments highlights personally meaningful glucose events. Start and stop points can be defined either directly as points in time or indirectly as points where the parameter, e.g. the glucose level, assumes specific values. It is preferred to use standard recording periods (15-minute or 1-hour segments) in order to ensure consistent display and allow for easy comparison of several shapes. Therefore it is advantageous to record glucose value-based intervals to the nearest hour. Usual sequences will have a length of 1 to 6 hours, according to the meaningful response time of the metabolism to an event. It is advantageous to limit the maximum recording time that may be saved as a sequence in order to ensure adherence of the data to an event context.

Preferably, a plurality of records may be automatically created subject to a number of selection parameters. For that purpose, a plurality of (essentially non-overlapping) segments each having a temporal start point and a temporal end point are selected from the chronological sequence of measurements, according to the selection parameters. For each selected segment a record is generated to be stored in the database.

This allows for easily creating a large number of records, each representing a glucose progression segment that relates to a certain given event (e.g. a meal). The selection parameters may comprise data that is already stored in the database, e.g. meal times entered before or the times of administration of a bolus received from an insulin delivering device. The segment may start directly with the triggering event or a certain time interval before (or after) that event, according to a respective selection parameter. The duration of a specific segment may be predefined (e.g. 4 hours) or the end point of the segment may be determined based on the actual progression (e.g. ended as soon as a certain glucose level or stability is reached). Further selection parameters may be used to restrict the generation to a certain time span (e.g. the last four days) or to certain times of the day (e.g. breakfast time).

The generated records may be automatically supplemented by additional data being already stored in the database (user meta-data, statistical information on the glucose progression etc.). Furthermore, the automatic generation may involve a step in which the user is prompted to enter additional information or to accept/decline an automatically created record or in which additional information is collected from further data sources such as further data gathering and/or storage devices (as discussed below). Furthermore, the automatic generation may involve a step in which it is checked whether a record relating to a specific event has already been created previously, in which case a new record would not be created again.

The automatic generation of new records may be continuously carried out during realtime operation of the system, i.e. as soon as certain criteria (corresponding to predefined selection parameters) are met a new record is generated. This ensures that essentially all relevant portions of the measured sequence are saved in the database in the form of meaningful event-related reports. The user will be able to adapt, to amend or to delete the automatically generated records at a later time. For that purpose, it may be useful if those automatically generated records that have not been actively confirmed (or amended or deleted) by the user are marked by a noticeable "NEW" flag.

Preferentially, the record stored in the database is supplemented with meta-data associated with the sequence of measurements, in particular with at least one of the following: a) a description identifying the sequence, supplied by a user; b) start and end points of the sequence; c) time and/or date information; d) complementary measurements of parameters measured in or on the human body; and/or e) user specified notes such as a log book commentary.

For later reference and comparison it is crucial that the context of the sequence of measurements previously stored is known. However, to date, event information (meals, sports etc) was often the hardest patient information to capture. The inventive method provides a simple tool for people to record data associated with specific events, leading to better self-management as well as improved analysis of CGM data by HCPs. It also supports the physician to interpret retrospective CGM data by providing a much greater understanding of cause and effect than achievable with raw data alone. Some of the meta-data listed above may be queried from the user (e.g. the description); other may be automatically generated and stored with each record (e.g. the time and/or date information). The meta-data may include user markings of individual records such as "typical record" (template), "abnormal record", "good", "bad" etc.

Additionally, if available to the system, at least part of the meta-data is automatically obtained via a communication link from one or more data gathering and/or storage devices such as insulin delivering devices, blood glucose meters, cellular phones, personal digital assistants (PDA) or personal computers. Subsequently, the relevant obtained data is preferably automatically stored with the record in the database. Relevant data includes any data that is associated with the recorded event and that relates to the same time and date as the sequence of measurements. The mentioned data gathering and/or storage devices may e.g. provide information about the timing and the rate of an insulin application, about the results of individual blood glucose measurements, about activities of the user, medication, mood, travel, menstrual period etc. Automatically gathering information that may be relevant in connection with the stored event facilitates subsequent interpretation of the parameter progression associated to the event by the user or its HCP.

Advantageously, the stored records are editable and/or manageable by the user, in particular in such a way that the user is able to do at least one of the following: a) editing meta-data; b) saving records at a specified location, in particular in user-definable folders; c) recalling records; d) searching records; e) sorting records; f) deleting records; g) exporting records; and/or h) comparing records.

This enables the user to highly customize the database and to facilitate the retrieval of stored data. Records (or shapes) may e.g. be grouped by event type. The user is able to setup custom event types and/or groups that can be created in addition to pre-defined types. It is important to note that the stored time segment of the sequence of measurements (source data) itself cannot be edited by the user, in order to avoid corruption of the basic data.

The user interface is preferably designed in such a way that thumbnail views of shapes characterizing a given record are displayed with a file name such that already the selection of a record may be done on a graphical level. Additionally, the markings provided by the user ("template", "good", "bad" etc.) may be displayed, e.g. in the form of icons or a color coding. Previous versions of a certain event (e.g. "pizza for lunch") can be easily accessed for comparison (where preferably the most recent event is default). Multiple recordings of similar events are encouraged. Because this comparison of personal response to like events has a valuable learning effect. Optional details concerning a certain event can be appended and amended at any time.

All these possibilities enable the user to improve his or her individual knowledge in the practice of self-management of diabetes. Embodiments of the invention do not rely on a theoretical model for diabetes, universal standards of care, or generalized medical guidelines. The degree of individualization is one of the most important advantages of the invention, as different people with diabetes react differently—even to the same foods and therapies—especially under real life conditions of overlapping meals, stress, disease staging, variable physical activity, medication, travel and hormonal changes.

In order to facilitate the comparison of two or more sequences, it is preferred that measurements of a first sequence and measurements of a second sequence (and possibly further sequences) stored in the database may be simultaneously graphically displayed.

It is also advantageous if measurements of a segment stored in the database and a real-time sequence of measurements may be simultaneously graphically displayed, whereas the graphical representation of the segment is placeable at a desired location along a timeline of the real-time measurement sequence.

The displayed sequences may be time-shifted according to the comparison needs, but always retain their original date/timestamp. This allows for easy comparison of the effect of different instances of similar events (as "pizza for lunch") or of different events (as "pizza for lunch" compared with "pizza for dinner" or "pizza for lunch" with "pasta for lunch", respectively).

In this respect, the graphical representation of the data is crucial for enabling everyone to develop a feeling for his body's reactions on specific events. This is also because these reactions, represented by the sequence of values of the measured parameter, are best understood when they are associated with events or circumstances that are personally meaningful to the patient. This is achieved by the combined process of recording continuous glucose data, highlighting and storing meaningful data segments, and making appropriate data comparisons.

For example, one embodiment according to the invention enables the use of continuous glucose monitoring to compare individual response to a known meal challenge. Meal-response experiments that are repeated on more than one occasion, such as "pizza for lunch," empower the patient and their doctor to make meaningful CGM data comparisons; and to thereby evaluate what is for the patient, personally, the metabolic significance of having pizza for lunch. If the patient's glucose response to similar events is indeed similar, the patient receives positive feedback about their level of control and self-awareness. If the patient's glucose response is not similar, the patient and physician can ask important questions of causality, such as "what other variables besides food might have caused the glucose response to be different?" Perhaps the reason comes from variations in the amount or timing of an insulin bolus; or consumption of very different types or quantities of food prior to the meal experiment in question. What is important is that CGM is a rich source of information that enables comparisons of event-based glycemic response. The ability to compare event-based glycemic response is highly valuable for people with diabetes and their physicians. The same methods of comparison can be used to improve knowledge about exercise events, travel, hormones, stress, etc.

By-and-by the user's data-base is built up and at some time it will contain a certain number of records, where preferably the records relating to "typical" (and well) responses of the user's body to a given challenge (e.g. a certain meal) are already marked by the user (or its HCP) as "template records"; these are idealized event-response curves and/or typical event-response curves. Faced with the same challenge at a later date, the user may display the shape corresponding to the template record on the timeline of the real-time measurement sequence, aligning the start of the shape with the timing of the current event. Subsequently, the user may currently compare on the display the current progression of his glucose level with the stored typical and well response. As long as the progression essentially follows the earlier event, the user may assume that everything is okay. If there is a substantial deviation, the user may think e.g. about performing a bG measurement in order to decide about countermeasures.

An embodiments of the inventive provides shapes in order to facilitate visual recognition, comparison, and differentiation of CGM metadata. Simple, consistent graphic conventions are essential to forming a meaningful visual vocabulary. In this respect, relative comparisons are preferred to absolute values. However, all measurements being simultaneously displayed should be displayed on equal value and time scales, i.e. X and Y scales (e.g. time and glucose resolution) must be consistent for displaying all shapes, because relative distortion between displays, especially the use of different aspect ratios, undermines meaningful analysis and comparison—if the aspect ratio is changed the shape is graphically distorted. It is even preferred that the value and time scales of the displayed shapes are always the same ones, ensuring that even shapes may be easily compared that are not displayed simultaneously. Setting up such a rigorous convention furthers the acquisition of the self-management skills and avoids misunderstandings on the side of the user. The most effective scaling for meaningful CM pattern analysis depends on the patient and should be determined through statistical analysis and validated by user testing.

If the user interface features thumbnail views, these views are preferably also scaled proportionally to the preset value and time scales, i.e. the thumbnail shapes are scaled-down representations of the usually displayed shapes. This kind of "uniform scaling" does not change the shape itself but only its size. This allows for comparing thumbnail shapes among each other as well as with the normal, bigger shapes. Furthermore, the recording duration of a sequence can be readily recognized from the thumbnail shape itself.

Preferably, an embodiment according to the inventive features a real-time mode in which the sequence of measurements is continuously dynamically supplemented with real-time measurements and in which the display of the measurements and the stored record are accordingly continuously updated. This allows for real-time monitoring of the actual performance of the parameter and for comparison with earlier sequences. Advantageously, a shape comparison may take place on the real-time timeline, e.g. by superimposing a stored shape on the real-time timeline. The current glucose value and bG trend may be further indicated on the real-time display.

Preferentially, an embodiment according to the inventive allows for automatic comparison of the sequence of measurements with sequences previously stored in the database, the comparison involving graphical, statistical and/or meta-data characteristics of the sequences. This automatic comparison step may be based on pattern recognition or on other methods such as known statistical methods etc. This allows for automatically providing the user with information about records that are already stored in the database and that match e.g. the current performance of the parameter. Furthermore, automated prompts for comparison or recording become possible as the program learns to detect patterns from accumulated personal data.

In order to improve data management and display, an embodiment according to the inventive advantageously comprises the further steps of collecting a number of measurements belonging to a given time span and of averaging the collected values in order to build an average value to be displayed. It is usually not necessary for the user to have glucose level information with a temporal resolution of 1 minute or less. On the contrary, variations of the measured parameter on such a scale may distract from the physiologically important aspects that usually happen on a 5-30 minutes scale. For standard CM data analysis the clinically relevant interval is about 15 minutes. However, if the measuring frequency is higher the large number of measurements may be averaged in order to simplify the graphical display and to emphasize general trends. In any case, the most effective time/glucose resolution for meaningful CM pattern analysis should be determined through statistical analysis and validated by user testing.

Preferably, the averaged value is not only displayed but also stored in the database. This ensures consistent data recording independent of the type or configuration of the continuous glucose measurement device.

Additionally, the initial sequence of measurements may be stored in the database. This allows for re-calculating the averages if e.g. the temporal resolution is subsequently changed. As the initial values are needed only rarely, it may be preferred that the initial values are regularly transferred to a backup media (such as a mass storage of a personal computer) in order to keep the memory requirements on the user device low.

The usefulness of the displayed shape may be even improved if interpolated values of the parameter corresponding to intermediate times, i.e. between measurements or between averaged values, are calculated. This way, a smooth curve segment is generated. This is especially useful in combination with the averaging process described above: The averaging process eliminates unnecessary short-time information leading to a "stepped" progression of the recorded parameter values, the subsequent interpolation smoothes out the "steps" and provides smooth curve segments. The smooth curves corresponding to different events may be more easily compared than stepped diagrams or curves showing short-time details.

Other advantageous embodiments and combinations of features come out from the detailed description below and the totality of the claims.

BRIEF DESCRIPTION OF THE DRAWINGS

The drawings used to explain the embodiments show.

In the figures, the same components are given the same reference symbols.

DETAILED DESCRIPTION

Figure 1:
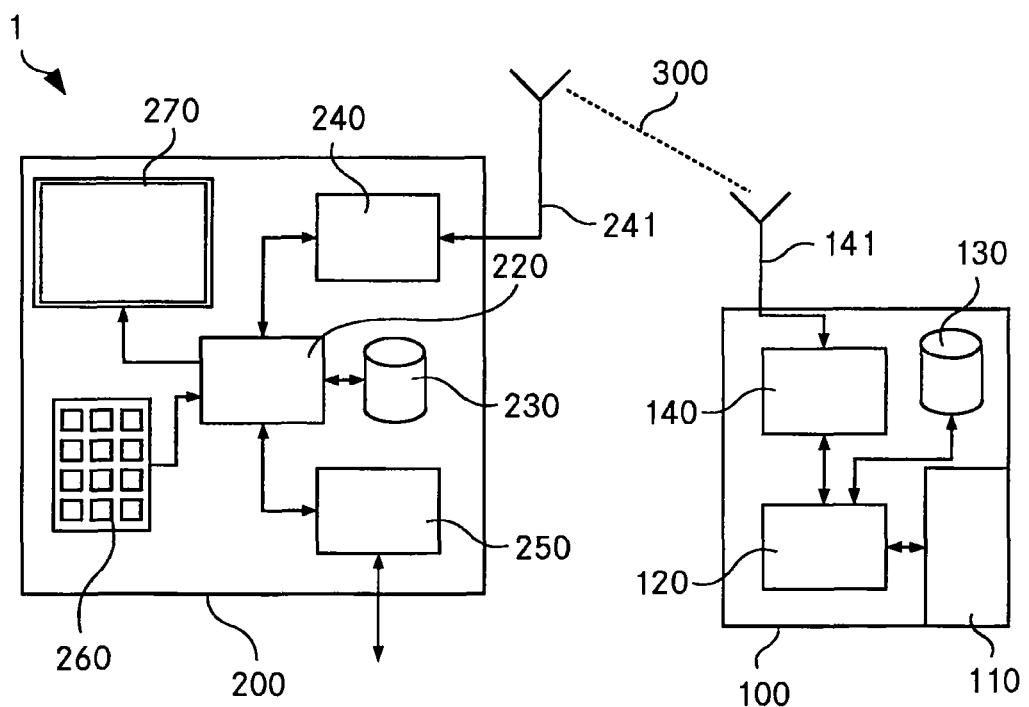
FIG. 1A schematic representation of an inventive system for processing a chronological sequence of measurements of a time dependent parameter measured in or on the human body.

The FIG. 1 is a schematic representation of an inventive system for processing a chronological sequence of measurements of a time dependent parameter measured in or on the human body, namely of the glucose level (e.g. the blood glucose (bG) level). The system 1 comprises a glucose measuring device 100 as well as a computing and display equipment 200. The two devices are linked by a wireless RF connection 300.

In the given example, the glucose measuring device 100 is to be placed on a human body and continuously measures glucose values in interstitial fluid by means of an electro-chemical (alternatively: photometric) glucose sensor 110. The measuring device 100 further comprises an extra corporal part including a central processing unit (CPU) 120, a storage 130 connected to the CPU 120 and an interface unit 140. The CPU 120 controls the sensor 110 and periodically stores the blood glucose value that is actually measured in storage 130. Suitable frequencies for taking measurements are from 10 (i.e. a measurement every six minutes) to 600 (i.e. a measurement every 10 seconds) measurements an hour. Periodically, the measurements stored in storage 130 are transmitted to the glucose measuring device 100 by means of the wireless RF connection 300. For this purpose, the data to be transmitted is first transmitted to the interface unit 140 by the CPU 120. The interface unit 140 pre-processes the data to be sent; this pre-processing step may include encryption of the data. Furthermore, the interface unit 140 includes a transceiver linked to an antenna 141.

The RF signal is received by an antenna 241 of the computing and display equipment 200. This equipment further comprises an interface unit 240 connected to the antenna, including a transceiver as well as a processing stage for processing the received signals as well as signals to be transmitted (see below). The equipment 200 is controlled by a central processing unit (CPU) 220 which is connected to a storage 230, a further interface unit 250, a user input device 260 and a display 270. The received measurements may be stored in storage 230 as well as displayed on the display 270 controlled by the CPU 220. By means of the further interface unit 250 the computing and display equipment 200 may be linked to further electronic devices such as a Personal Computer (PC) of the patient or the health care provider or further data gathering and/or storage devices such as insulin delivering devices, blood glucose meters, cellular phones, personal digital assistants (PDA) etc. This allows for automatically obtaining at least part of the meta-data (timing and rate of an insulin application, results of individual blood glucose measurements, activities of the user etc.) to be stored in the database.

Besides for transmitting measured values from the glucose measuring device 100 to the computing and display equipment 200 the wireless RF connection 300 also serves for transmitting control data from the equipment 200 to the measuring device 100, e.g. to change the measurement frequency or to initiate if the transmission of the data stored on the glucose measuring device 100, if the transmission is usually initiated by the equipment 200 (polling mode).

The computing and display equipment 200 may be implemented by a personal digital assistant (PDA, including portable music/multimedia players), a personal computer, a cellular or smart phone, a specific remote control for an infusion pump, an analyte measuring device such as a glucose measuring device such as e.g. a hand held glucose meter, more preferably a strip based glucose meter, or combinations thereof. Some of these devices usually comprise most or all of the components described above: as an example, a PDA usually features wireless as well as wire-based connection interfaces (e.g. Bluetooth and USB, respectively), a rather powerful CPU, storage means (e.g. internal Flash storage and replaceable memory cards), user input devices (keys, touchpad, touchscreen etc.) as well as a display (e.g. a high resolution color LCD display). Therefore, in these cases it is sufficient to provide a specific software adapted to the actual equipment 200 that provides the desired functionality of the inventive system.

Figure 2A:
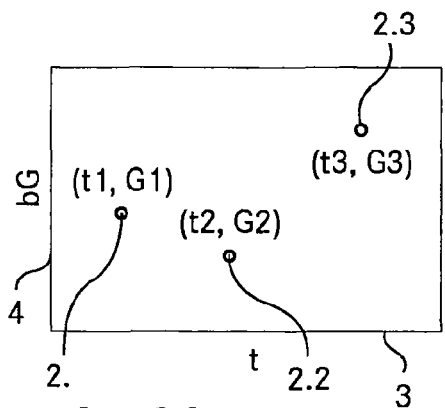
FIG. 2A-F a schematical representation of the inventive conversion of time-series glucose data into an easily perceivable shape.
Figure 2B:
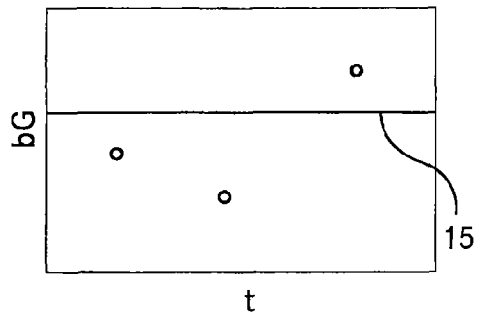

FIGS. 2A-F are a basic schematical representation of the inventive conversion of time-series glucose data into an easily perceivable shape. In order to build such a shape a least three time-value data pairs (t, G) 2.1, 2.2, 2.3 corresponding to different times are needed (FIG. 2A). The first data pair 2.1 relates to the temporal start point of the shape, the last data pair 2.3 relates to its end point. The number of data pairs 2.2 in between may vary according to the length of the time interval and the desired resolution. The data pairs 2.1, 2.2, 2.3 relate a given point in time to the blood glucose (bG) value measured at that moment. The data pairs 2.1, 2.2, 2.3 are represented in a two-dimensional coordinate system having time on the horizontal axis 3 and the bG value on the vertical axis 4. In order to build a shape, a reference line 15 corresponding to a bG target value is needed (FIG. 2B). The bG value corresponding to the horizontal reference line 15 may be set by the user or its HCP, respectively.

Figure 2C:
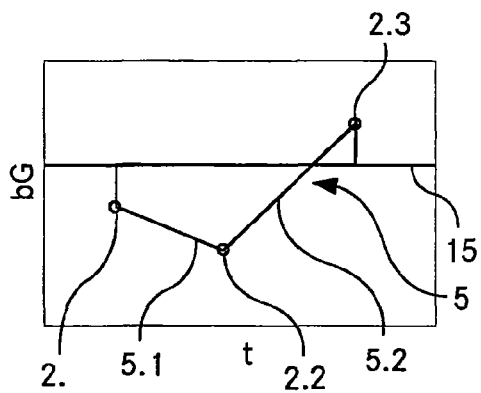
Figure 2D:
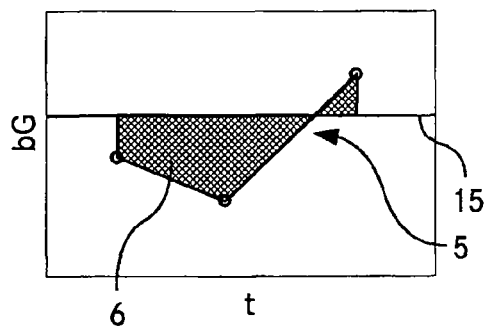
Figure 2E:
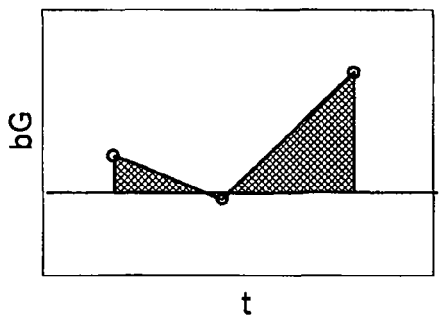
Figure 2F:
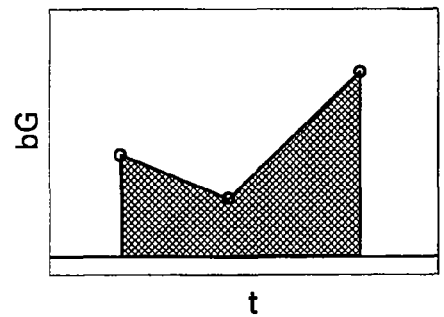

Next, the points in the coordinate system corresponding to consecutive data pairs 2.1, 2.2, 2.3 are connected to each other by lines 5.1, 5.2 building up a curve 5 (FIG. 2C). Subsequently, the geometrical area 6 delimited by the curve 5 and the reference line 15, i.e. the "area under the curve" on both sides of the reference line 15, is highlighted, e.g. by filling with a certain color (FIG. 2D). As can be seen from FIGS. 2D, 2E and 2F, the visual appearance of the shape will be different if the position of the reference line 15 is changed.

Figure 3:
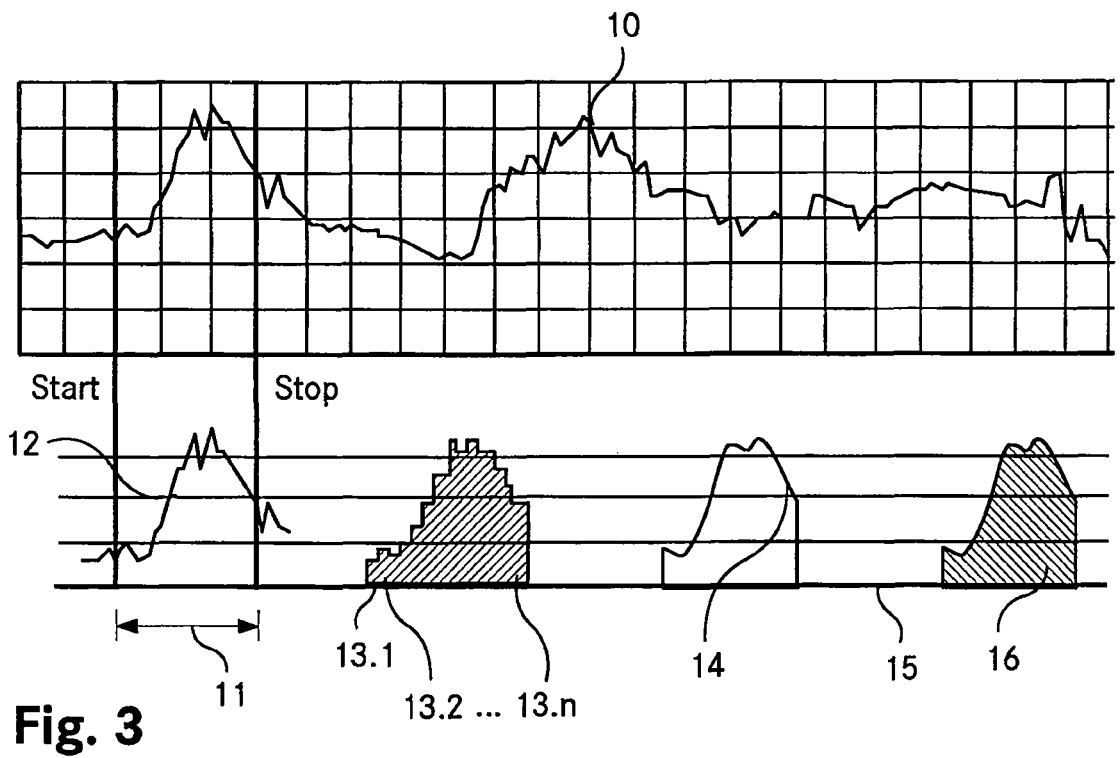
FIG. 3 a schematic representation of the processing of a chronological sequence of measurements.

The FIG. 3 is a schematic representation of the processing of a chronological sequence of measurements transmitted by the glucose measuring device 100 and initially stored in the storage 230 of the computing and display equipment 200. The measurements, represented by a number of time-value data pairs building up the curve 10, have a high temporal resolution such as 20 measurements per hour (one stored measurement every three minutes) or more. First of all, the user defines an interval 11 (see below) that represents a certain event and the consequences of this event on the blood glucose level. The duration of the interval 11 is e.g. three hours. The measurements belonging to that interval 11 are isolated (curve 12).

In a further step, this data is averaged to segments 13.1 ... 13.*n* of a given length (e.g. 15 minutes), i.e. in the given example five measurements at a time are averaged and the average represents the blood glucose value for the respective segment 13.1 ... 13.*n*. This step suppresses information on short time scales.

Next, a smooth curve 14 is generated from the averages 13.1 ... 13.*n* by means that are known as such (interpolation by polynomial fits, splines etc.). Finally, in order to accentuate the curve shape the area between the curve 14 and the reference line 15 is displayed as a "solid" shape 16. This confined, simplified shape 16 is much better suited for a visual comparison with other shapes 16 of this kind than is the extensive and (over-) detailed initial curve 10.

Figure 4:
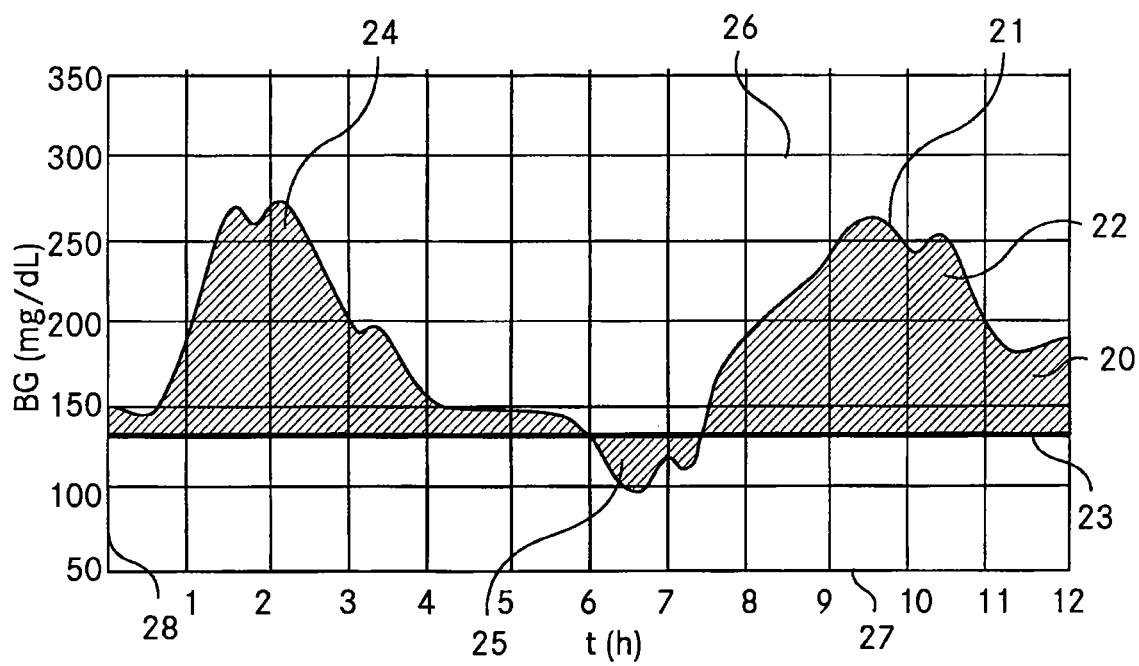
FIG. 4 a schematic representation of a shape as displayed on a user interface display.

The FIG. 4 is a schematic representation of a shape as displayed on a user interface display. The shape 20 is constituted by a curve 21 obtained from the raw measurements by averaging and smoothing as described above as well as by the areas 22 lying between the curve 21 and the reference line 23. These areas 22 are highlighted by solid coloring. The areas 22 lying above the reference line 23 may be read and memorized as "mountains" 24, whereas the areas 22 lying below the reference line 23 may be read and memorized as "valleys" 25. The shape 20 is displayed in a wire grid 26 and the absolute values of the curve 21 may be read from the axes 27, 28 labeled with time and glucose level values respectively.

Figure 5:
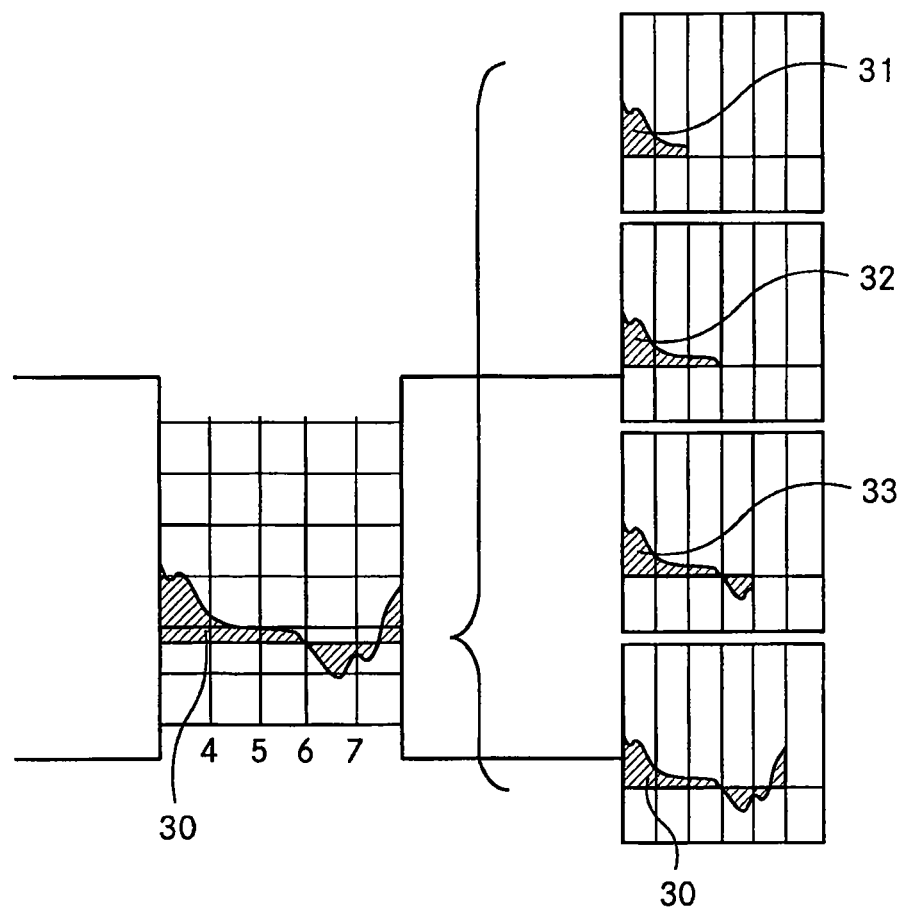
FIG. 5 a diagram visualizing the presentation of shapes corresponding to sequences of different lengths.

The FIG. 5 is a diagram visualizing the presentation of shapes corresponding to sequences of different lengths. For the purpose of illustration, an example shape 30 having a length of five hours is chosen. Independent of whether the full shape 30 is to be displayed on the user interface or only a 2-hour segment 31, a three-hour segment 32 or a four-hour segment 33, the scaling of the time as well as of the glucose value axis is always the same, irrespective of whether these shapes are displayed simultaneously or one after the other. This ensures easy comparison between different shapes. Once typical maximum lengths of sequences (e.g. 6 hours) and usual fluctuations of the patient's glucose level (e.g. 50-350 mg/dl) are known the scale should be fixed and not changed anymore. Thereby, after some familiarization, the user will be able to grasp the essential aspects of a shape at a glance without having to look at e.g. the axis labeling.

Figure 6:
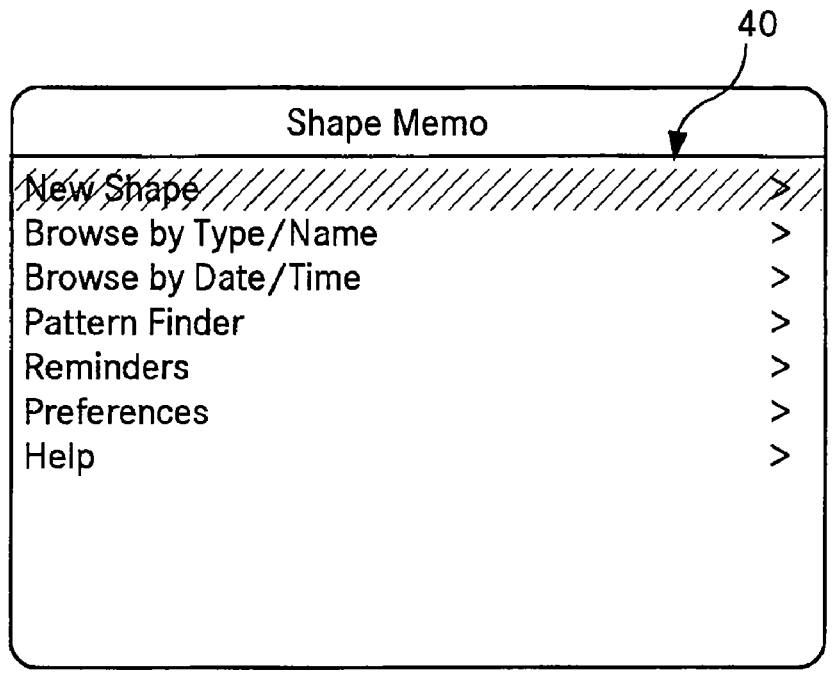
FIG. 6 the shape menu of the graphical user interface, displayed on a computing and display equipment.

The FIG. 6 shows the shape menu of the graphical user interface, displayed on a computing and display equipment. In the given example, the graphical user interface resembles the Apple-Ipod interface. Correspondingly, choosing from menu options or adjusting parameters can be effected using a Clickwheel. However, other input means such as a touch screen, a touch pad or conventional keys and/or other user interfaces (such as Microsoft Windows) are appropriate as well. The corresponding menu structure may be realized on other equipment such as PDAs, mobile/smart phones etc.

The menu 40 shown in FIG. 6 allows for choosing from the following options: a) New Shape; b) Browse by Type/Name; c) Browse by Date/Time; d) Pattern Finder; e) Reminders; f) Preferences; and g) Help.

Figure 7A:
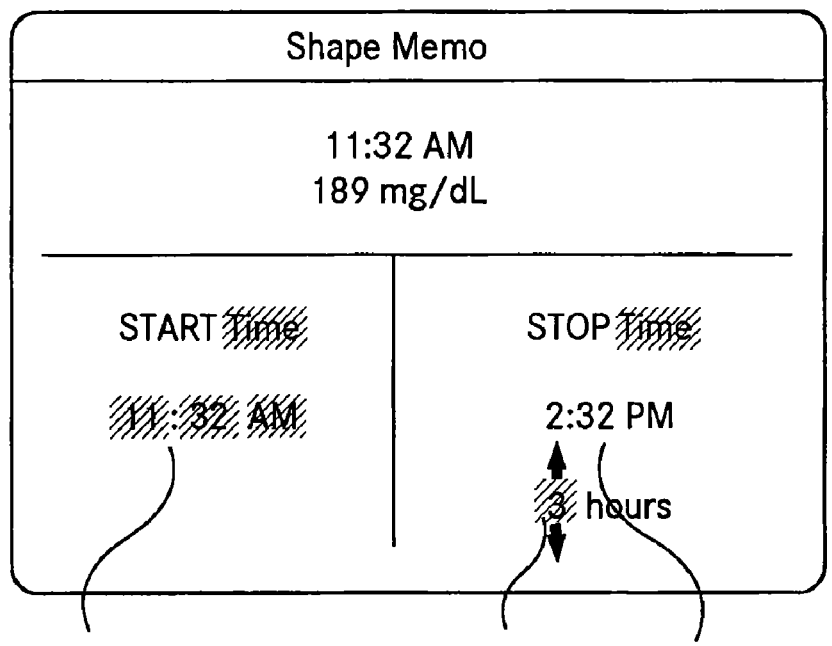
FIG. 7A, B user dialogues for defining a time interval by setting points in time or entering a glucose level for defining the endpoint of the interval.
Figure 7B:
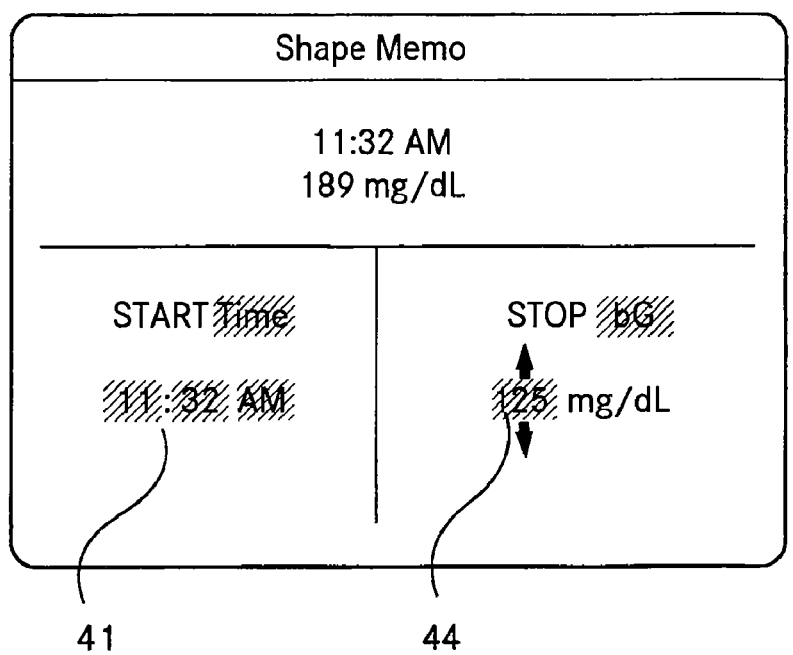
FIG. 7C a user dialogue for parameterizing the automatic creation of one or a plurality of new shapes.
Figure 7C:
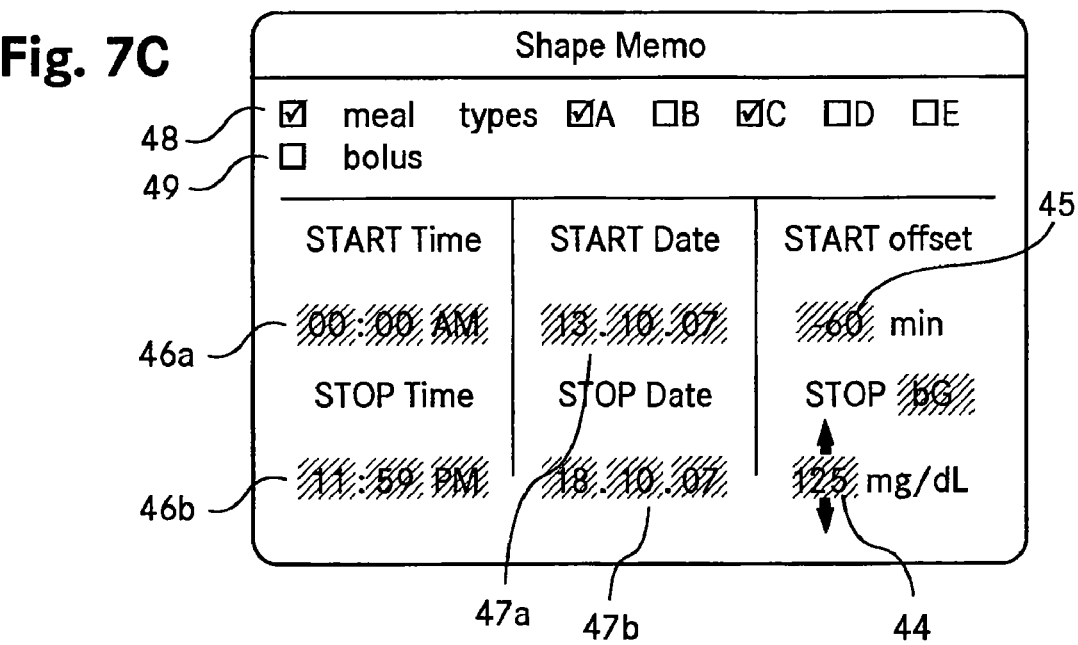

A new shape may be generated by choosing option a). The FIGS. 7A-7C show three different options for defining the time interval in which the measured blood glucose values will contribute to the shape. The user dialogues displayed in FIGS. 7A, 7B relate to the creation of a single new shape. Both dialogues show the current time ("11:32 AM") as well as the current blood glucose value ("189 mg/dL"). By default, the start time (starting point of the interval) 41 for the shape to be generated corresponds to the current time ("11:32 AM"). Via the user dialogue displayed in FIG. 7A the stop time (endpoint of the interval) 42 ("2:32 PM") may be defined by adding a number of full hours 43 ("3 hours") to the start time 41, i.e. by choosing the length of the interval that contributes to the shape. Via the user dialogue displayed in FIG. 7B the stop time is defined by indicating a preset blood glucose (bG) value 44 ("125 mg/dL"): The interval will end as soon as this value is reached. Due to the fact that only one value (hour offset 43 or bG value 44, respectively) has to be chosen, defining the interval is very simple and fast. In the course of generating a new shape the user will be prompted for a name. The name should be a short but meaningful description of the corresponding event (e.g. "Pizza" or even "Pizza for lunch") and will serve as a kind of "file name". It is one of the prime identifiers of the event (besides further meta-data such as time and date, amount of carbohydrates, rate of an insulin bolus etc., see below).

The user dialogue displayed in FIG. 7C relates to the automatic creation of one or a plurality of new shapes. It enables the user to enter a number of selection parameters which are subsequently used to generate new shapes corresponding to portions of the measured blood glucose progression that match the selection parameters. Firstly, the user may define a start date 47*a* and a stop date 47*b* as well as a start time 46*a* and a stop time 46*b*. Only those portions of the progression are taken into account which lie both within the entered dates and within the entered times. In the example given in FIG. 7C all events will be considered that happen (or happened) on any of the days of 13 to 18 Oct. 2007. The chosen interval(s) may lie completely in the past, completely in the future or covering the present time. Accordingly, the data collection will may be based entirely on data that has already been collected or it may involve future data, in which case the corresponding records will be created in real time as soon as the required data is available.

Furthermore, the user defines the event types that will be taken into account. In the current example, meals (checkbox 48) of predefined types A and C will be considered, whereas meals of types B, D and E as well as bolus administrations (checkbox 49) will not. Finally, the user chooses the shape start offset 45 (in the current example 60 minutes earlier than the triggering event) as well as the stop time of the interval contributing to the shape. In the current example the stop time is defined by indicating a preset blood glucose (bG) value 44 ("125 mg/dL"): The interval will end as soon as this value is reached.

Further meta-data may be gathered by querying the user or from external devices such as insulin delivering devices, blood glucose meters, cellular phones, personal digital assistants (PDA) etc. or personal computers and automatically stored in the database.

In order to obtain standardized shapes consisting of 15-minute segments the glucose based interval is recorded to the nearest hour. In either way, the maximum recording time is limited to 6 hours. This ensures adherence to the event context and defines a maximum length for displaying a shape, which is important in view of displaying the shapes with predetermined fixed scales.

By choosing options b) and c) from the shape menu as shown in FIG. 6 shapes stored earlier in the database may be retrieved, employing different criteria. The shapes may be browsed by type and name (see FIG. 7, comment below) or by date and time.

Option d) allows for finding patterns, i.e. earlier shapes that match a certain shape. Option e) allows for defining, editing and deleting reminders. These reminders may be triggered by a number of events: the lapse of a certain time period (count down), a certain point in time, reaching a certain glucose level or predefined events regarding the glucose level (passing of a maximum/minimum, exceed a bG gradient etc.) The reminders may have a mere warning function or they may be displayed in combination with a prompt that invites the user to provide information or that proposes certain actions (as starting to record measurements for generating a new shape). By choosing option f) certain user preferences (display brightness and contrast, colors, screen saver, graph options etc.) may be edited. Finally, option g) displays a help menu, providing access to various documentation about using the software.

Figure 8:
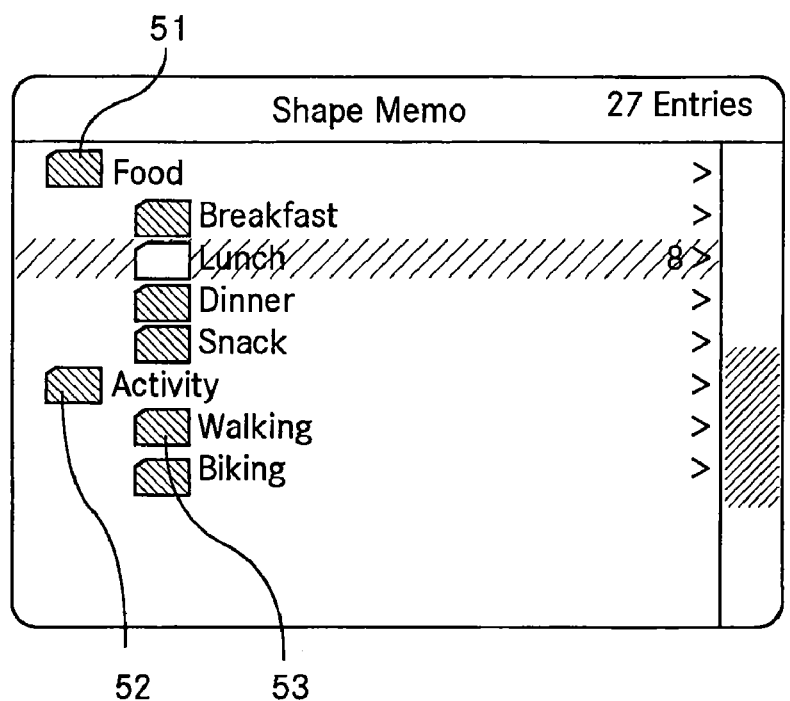
FIG. 8 the directory structure for storing and retrieving shapes into and from the database, respectively.

FIG. 8 shows the directory structure for storing and retrieving shapes into and from the database, respectively, where the shapes are hierarchically grouped by event type.

On a first (top) level the events are divided into two groups ("Food", "Activity") containing events 51 that are related to ingestion and events 52 that are related to physical activity. On a second level, the events are further classified into specified event types 53 that relate to specific contexts (such as in the given example breakfast, lunch, dinner, snack for ingestion events, as well as walking, biking for physical activity events). The user is free to create further, custom event types and/or groups.

Figure 9:
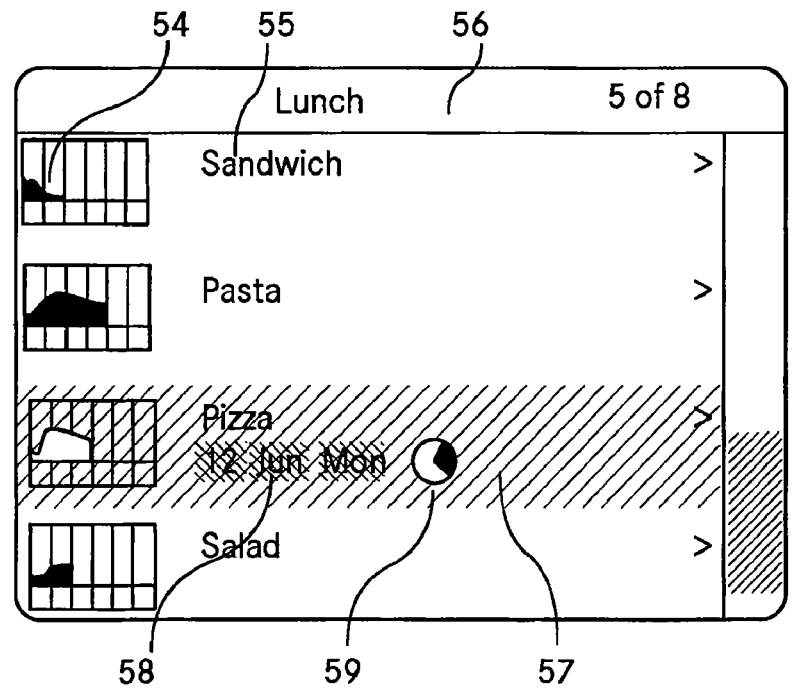
FIG. 9 the thumbnail representation of a shape within a given directory.

Once a given event type directory is chosen, the contained records ("Sandwich, Pasta, Pizza, Salad") are displayed, as is shown in FIG. 9. This includes the display of a thumbnail representation 54 of every event within the given directory as well as of the names 55 assigned to all the displayed records. The title bar 56 shows the name of the directory that corresponds to the name of the event type ("Lunch"). For the record 57 that is currently highlighted additionally the date and weekday 58 ("12 June Mon") as well as the time and interval 59 of the latest recorded incident are displayed. The time and interval information 59 is given as a marked segment of a clock face. This allows for quickly identifying the relevant information.

Figure 10:
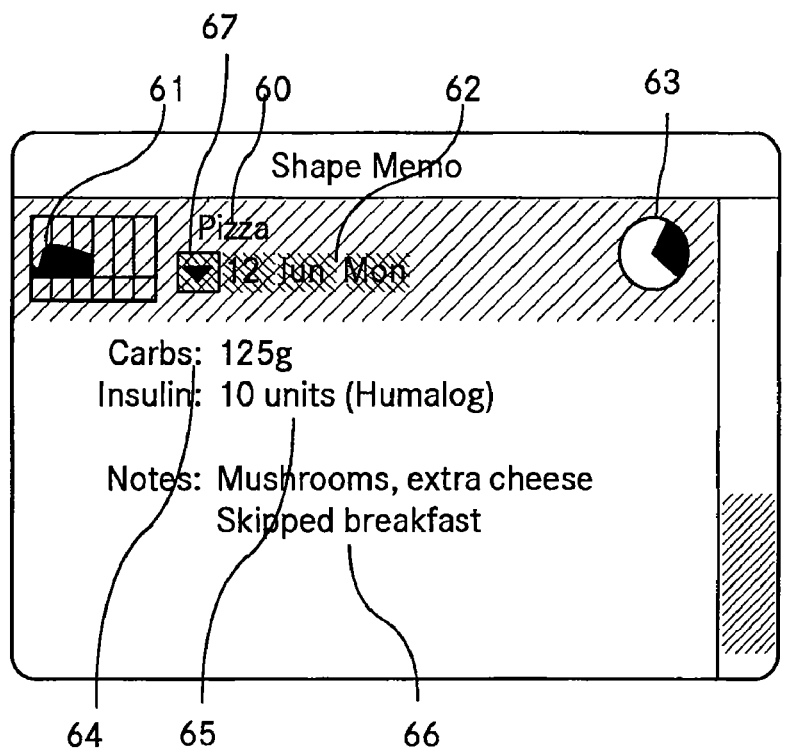
FIG. 10 the detailed view of a record.

FIG. 10 shows the detailed view of a record that appears once it has been chosen from the event directory displayed in FIG. 9. The detailed view shows the information discussed above in relation with FIG. 9, i.e. the name 60 of the record ("Pizza") as well as the shape 61, date/weekday 62 ("12 June Mon") and time/interval 63 of the incident that has been most recently recorded. In a lower part of the display additional information relating to the displayed incident is provided such as the amount of carbohydrates 64 of the meal ("Carbs 125 g"), the rate as well as the insulin type of an insulin bolus 65 ("Insulin 10 units (Humalog)") as well as notes 66 that are provided by the user (e.g. further information concerning the ingredients of the meal or concerning special circumstances, in the given example "Notes Mushrooms, extra cheese, Skipped Breakfast"). The notes may be provided or amended at any time. However, in order to ensure accurate information the user will be prompted for the information immediately after creation of the record.

By default the most recently recorded incident is displayed. However, previous incidents of the same event may be easily accessed by means of a pulldown menu 67. The shape corresponding to a specific incident that is considered by the user to be a typical and well reaction of his body to a specific challenge may be marked as a "template shape". These shapes are highlighted by a corresponding icon and may further be used in comparisons (see below, FIG. 12). Similarly, shapes that correspond to abnormal reactions may be marked as abnormal shapes.

Figure 11:
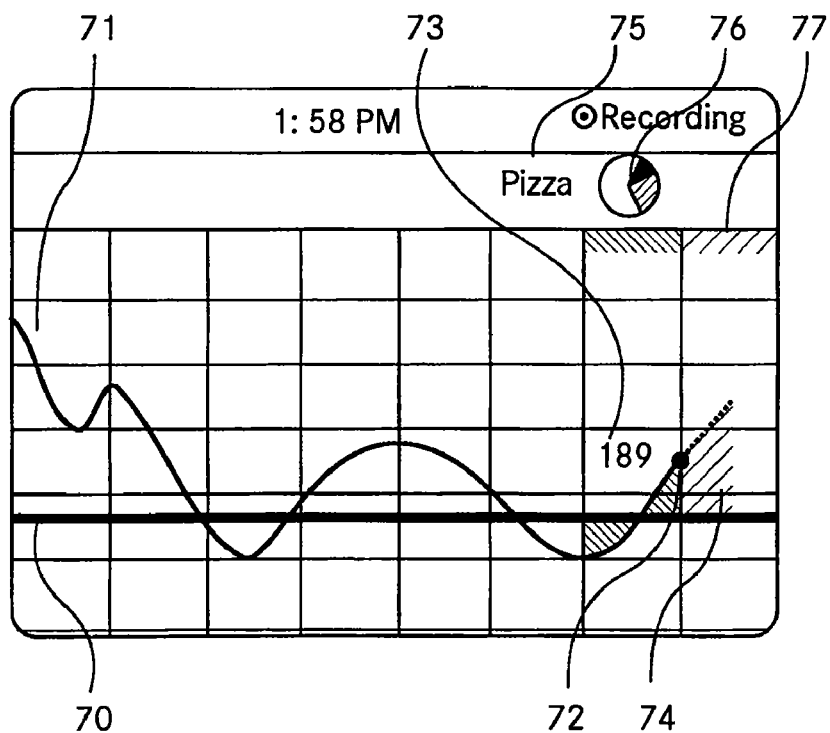
FIG. 11 the display in real-time mode of the system.
Figure 12:
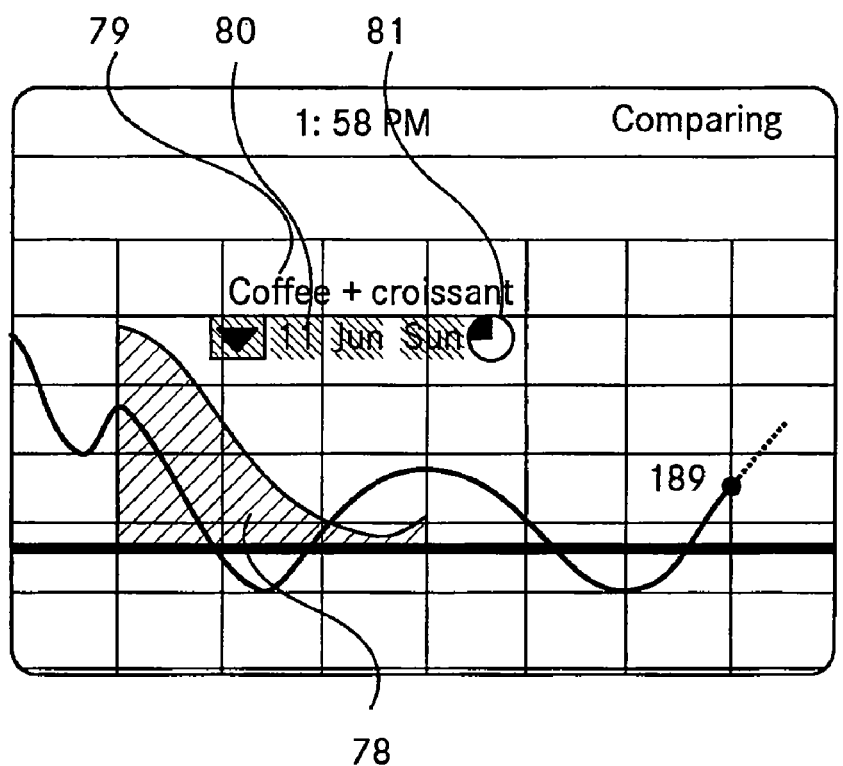
FIG. 12 the simultaneous graphical display of the real-time time line and a template shape.

The FIGS. 11 and 12 show the display in real-time mode of the system during the recording of a shape. FIG. 11 shows the real-time timeline including the reference line 70 corresponding to a target value of the patient's blood glucose level and a curve 71 indicating the progression of the bG level during the last hours. The scales of the axes correspond to the predetermined fixed scales mentioned above. A point 72 of the curve 71 representing the current value of the glucose level is marked and the current bG level 73 in mg/dl is stated in numbers ("189"). Based on a certain interval before the current time (which is also marked in the displayed graph) a bG trend 74 is calculated and displayed as well. Furthermore, the memo name 75 ("Pizza"), the recording interval 76 and a progression bar 77 showing the elapsed time of the interval versus the total time of the interval are displayed.

During recording of the shape (or at a later stage) the user may activate a comparison mode that allows for shape comparison in place on the real-time timeline (see FIG. 12). In comparison mode any saved shape 78 may be loaded into the real-time timeline, either manually or automatically. In manual mode, the shape to be loaded may be chosen from the usual menu structure as described in connection with FIGS. 8 and 9 above. Together with the loaded shape 78 its memo name 79 ("Coffee+Croissant") is displayed. The loaded shape 78 may be shifted along the real-time timeline according to comparison needs but it will always retain its original date 80 and timestamp 81 ("11 June Sun"). In particular, the user may select a template shape 78 that represents a typical and well response of the user's body to a specific challenge (such as "Coffee+Croissant"). Selecting these templates is facilitated by user-provided markings of corresponding database records (see above). Faced with the same challenge, the user may now display the shape 78 corresponding to the template record on the timeline of the real-time sequence, aligning the start of the shape 78 with the timing of the current event. Subsequently, the current progression of the blood-glucose level may be compared with the stored template response in order to detect anomalies.

In automatic mode, the database of saved shapes is searched for shapes that match the current bG progression as closely as possible. The comparison process may include a rating process where the similarity between the current real-time progression and every shape is rated (e.g. by calculating a sum of $\chi^2$-distances along the time axis).

Figure 13:
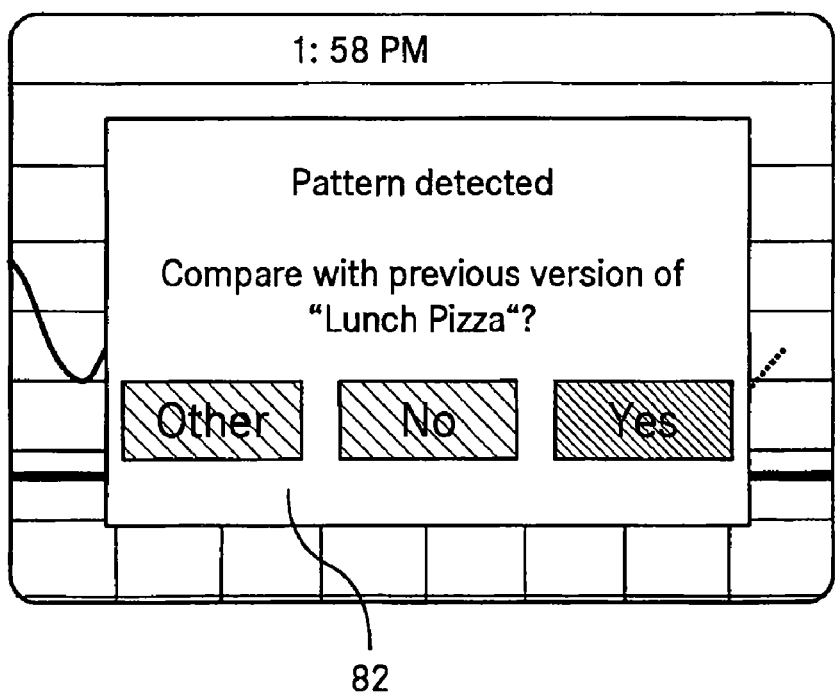
FIG. 13 the automatic comparison process.

FIG. 13 illustrates the automatic comparison process. A stored shape or the real-time progression of the blood glucose level may be compared to shapes previously stored in the database. If a matching shape is detected the prompt 82 displayed in FIG. 13 is displayed ("Pattern detected. Compare with previous version of "Lunch:Pizza"? Other/No/Yes"). The user has the possibilities of loading the corresponding shape into the time line ("Yes") or to display both shapes simultaneously, respectively (see below, FIG. 15), to search for another matching shape ("Other") or to cancel the search ("No"). The system will learn from accumulated personal data and the more data is stored in the database the better matches will be obtained.

Figure 14:
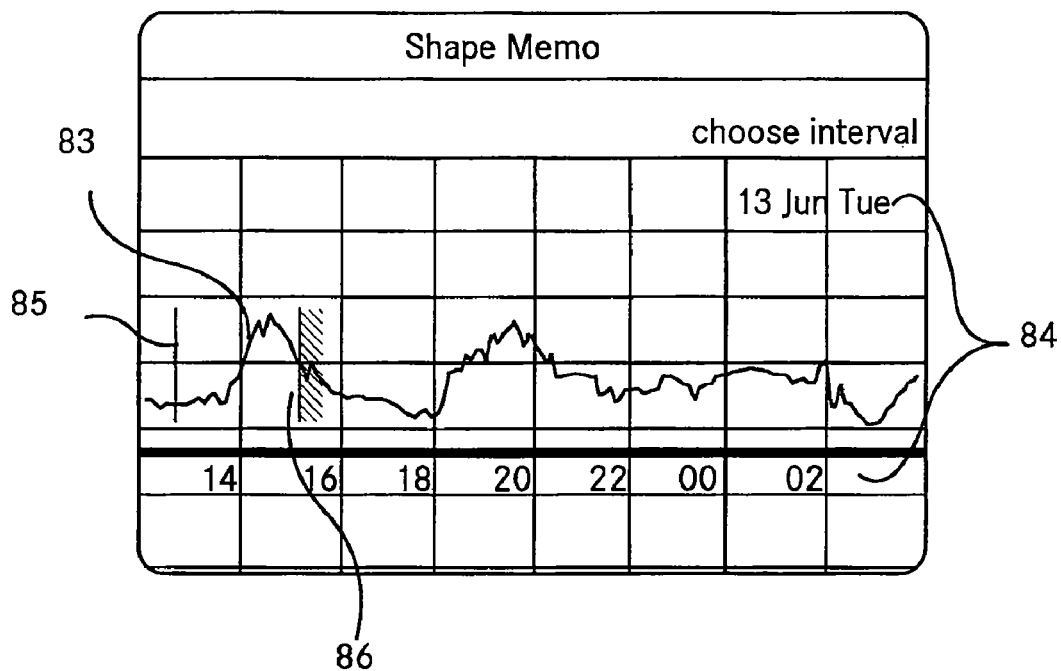
FIG. 14 the graphical user interface for choosing a time interval from pre-recorded data.

In one embodiment it is not only possible to define a time interval at its starting point as described above in connection with FIGS. 7A, 7B but also later on, during the interval or even after it has ended. For this purpose, the measurements received from the measuring device are continuously stored in the storage of the computing and display equipment, in such a way that the progression of the glucose level during a certain time span (e.g. 36 hours) before the actual time is always available. FIG. 14 shows the graphical user interface for choosing a time interval from that pre-recorded data. The progression of the glucose level is displayed as a curve 83, together with time and date information 84 ("13 June Tue", "14 16 18 ... 02"). By shifting a start bar 85 as well as and end bar 86 the time interval in which the measured blood glucose values shall contribute to a new shape may be defined by the user. In order to obtain standardized shapes consisting of 1-hour segments the chosen interval is extended to the next full hour. Again, the maximum recording time is limited to 6 hours, in order to ensure adherence to the event context.

After the user has defined the time interval a new shape is automatically generated as described above, in connection with FIG. 3. Subsequently, the user may amend the new instance with further information, such as a title and a description. Finally, the shape is stored in an event type directory (see above and FIG. 8) and assigned to an existing or new record.

The time span during which the progression of the physiological parameter is still available and accessible by the user is deliberately chosen to be limited to about 1-2 days, in order to ensure that the information supplied by the user relating to the time span and the corresponding event (food intake, physical activity etc.) is as correct as possible. In principle, it is possible to store information on the device that relates to longer time spans, however this information should not be eligible for generating new instances and records. It could however be valuable for the patient's HCP.

Figure 15:
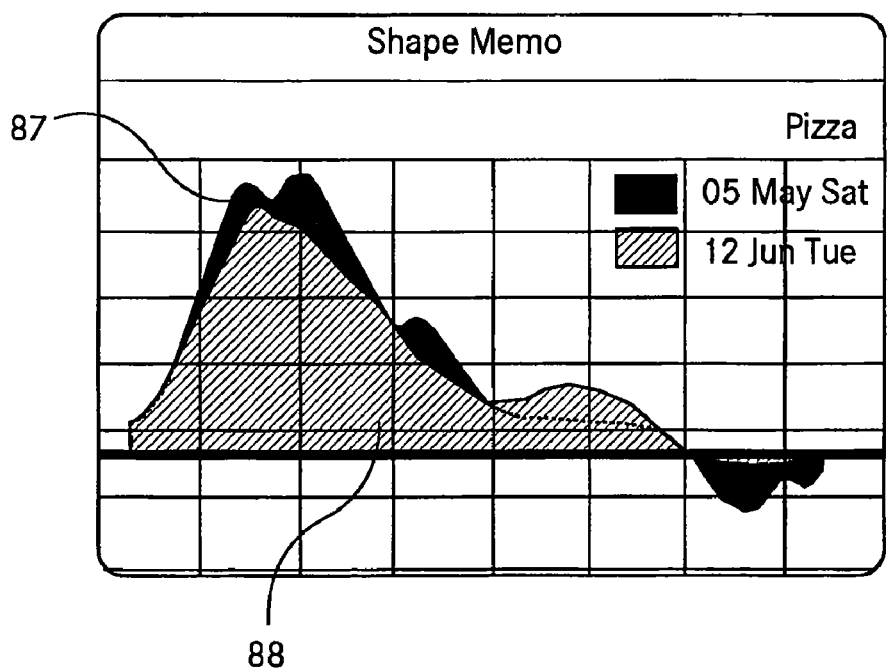
FIG. 15 the display view for the comparison of two shapes.

The comparison of an existing shape stored in the database with the current progression of the blood glucose level has been described above, in connection with FIG. 12. It is also possible to do comparisons between two shapes that are stored in the database. FIG. 15 is a view of the graphical representation for the comparison of two such shapes 87, 88. Both the shapes 87, 88 are displayed in a superposed manner, where the shapes are differentiated by different colors, patterns and/or hatchings. In the given example, a first shape 87 generated from a time span on 5 May (solid) as well as a second shape 88 from a time span on 12 June (hatched) are displayed. The first shape 87 is displayed in the background, whereas the second shape 88 is displayed in the foreground. In order to provide the user with the full information about both the shapes 87, 88, irrespective of whether a current value of the first or the second shape is higher, the boundary of the background shape 87 is indicated with a dashed line where the value of the background shape 87 is smaller than that of the foreground shape 88, where the background shape 87 is therefore hidden behind the other shape 88.

From the picture as represented in FIG. 15, the user may immediately identify commonalities as well as differences between the two shapes.

The system according to the invention will further provide the user and/or his or her HCP with the possibilities of a) editing meta-data, e.g. the title and description of a record; b) saving records at a specified location, in particular in user-definable directories as described above; c) recalling records for display; d) searching records according to different criteria (date, time, title, description etc.); e) sorting records according to different criteria (values of the bG level, date, time, duration, title, description etc.); f) deleting records; g) exporting records, e.g. via the further interface unit to a Personal Computer; and/or h) performing shape comparisons.

The invention is not limited to the embodiments described above. The functionalities itself as well as the graphical user interface may be modified in many ways. Particularly, they may be adapted to the computing and display equipment used, especially to its input means, kind of display, display size, computing power, memory size etc.

The continuous glucose measurements (CGM) are not restricted to measurements of the blood glucose (bG) level but may be directed to other glucose levels, such as e.g. glucose levels measured in the interstitial fluid.

In summary, it is to be noted that embodiments of the invention provide a method as well as a system for processing a chronological sequence of measurements of a time dependent parameter measured in or on a human body, in particular of a physiological glucose concentration, that enables the patient to improve his self-management skills concerning his therapy.

What is claimed is:

1. A method for processing a chronological sequence of measurements of a time dependent parameter measured in or on a human body comprising:
    storing a time segment of the sequence of measurements as a record in a database;
    automatically comparing the sequence of measurements with segments previously stored in the database, the comparison involving graphical, statistical or metadata characteristics of the sequence and of the segments, respectively; and
    simultaneously graphically displaying at least three of the measurements of the stored segment on a user interface display.

2. The method as recited in claim 1, further comprising defining a temporal start point and an end point of the segment and including measurements of the sequence lying in between said start point and said end point in the record stored in the database.

3. The method as recited in claim 2, further comprising creating automatically a plurality of records subject to a number of selection parameters, wherein a plurality of segments each having a temporal start point and a temporal end point are selected from the chronological sequence of measurements according to the selection parameters, and generating for each selected segment a record to be stored in the database.

4. The method as recited in claim 1, further comprising supplementing the record with meta-data associated with the time segment, in particular with at least one of the following:
    a description identifying the segment, supplied by a user;
    start and end points of the segment;
    time and/or date information;
    complementary measurements of parameters measured in or on the human body; and
    user specified notes such as a log book commentary.

5. The method as recited in claim 4, further comprising obtaining automatically at least part of the metadata via a communication link from one or more data gathering and/or storage devices selected from insulin delivering devices, blood glucose meters, cellular phones, personal digital assistants (PDA), and personal computers.

6. The method as recited in claim 1, further comprising accepting user input which facilitates at least one of the following: editing meta-data; saving records at a specified location in user-definable folders; recalling records; searching records; sorting records; deleting records; exporting records; and comparing records.

7. The method as recited in claim 1, wherein measurements of a first segment and measurements of a second segment stored in the database are simultaneously graphically displayed.

8. The method as recited in claim 7, further comprising displaying all measurements being simultaneously displayed on equal value and time scales.

9. The method as recited in claim 1, wherein measurements of a segment stored in the database and a real-time sequence of measurements are simultaneously graphically displayed, and said method further comprising placing the graphical representation of the segment at a desired location along a timeline of the real-time measurement sequence.

10. The method as recited in claim 1, further comprising continuously dynamically supplementing the sequence of measurements with real-time measurements and continuously updating the display of the measurements and the stored record accordingly.

11. The method as recited in claim 1, wherein the parameter is a glucose concentration measured by a continuous glucose measurement system.

12. The method as recited in claim 11, further comprising using a continuous glucose sensor device placed in or on the human body to provide measurements of glucose values in interstitial fluid and transmitting the measurements to a computing and display equipment selected from a PDA, a personal computer, a cellular or smart phone, a specific remote control for an infusion pump, an analyte measuring device, and combinations thereof.

13. The method as recited in claim 12, wherein the measurements are transmitted from the sensor device to the computing and display equipment by wireless communication.

14. A non-transitory computer-readable medium that stores a computer program comprising code means that when executed by a data processing system carry out each of the steps of method claim 1.

15. A system for processing a chronological sequence of measurements of a time dependent parameter measured in or on a human body, in particular of a physiological glucose concentration, the system comprising a computing and display equipment selected from a PDA, a personal computer, a cellular or smart phone, a specific remote control for an infusion pump, an analyte measuring device, and combinations thereof, the computing and display equipment comprising a database storing a plurality of chronological sequences of measurements of the time dependent parameter and the computing and display equipment being designed and controlled in such a way that at least three of the measurements of a sequence stored in the database is simultaneously graphically displayable on a user interface display, wherein the system automatically compares the sequence of measurements with segments previously stored in the database, the comparison involving graphical, statistical or metadata characteristics of the sequence and of the segments, respectively.

16. The system as recited in claim 15, wherein the computing and display equipment comprises means for receiving user input, and means for editing and managing sequences stored in the database, depending on the user input.

17. The system as recited in claim 15, wherein the system comprises a continuous glucose sensor device to be placed in or on the human body in order to measure glucose values in interstitial fluid and in that the computing and display device comprises an RF receiver which receives measurements performed by the sensor device.

18. A method for processing a chronological sequence of measurements of a time dependent parameter measured in or on a human body comprising:
  storing a time segment of the chronological sequence of measurements as a record in a database;
  simultaneously graphically displaying at least three of the measurements of the stored time segment on a user interface display, wherein values of the at least three measurements are displayed in a time-value coordinate system as time-value data pairs in relation to a reference line; and
  connecting temporally adjacent data pairs to build a curve and highlighting a geometrical area between the curve and the reference line to build a characteristic shape corresponding to the stored time segment.

19. The method as recited in claim 18, wherein the reference line corresponds to a reference value, such as a target or household value, of the parameter.

20. The method as recited in claim 19, further comprising accepting a user input changing the reference value and updating all data stored in the database according to the changed reference value.

21. A method for processing a chronological sequence of measurements of a time dependent parameter measured in or on a human body comprising:
  storing a time segment of the chronological sequence of measurements as a record in a database;
  collecting a number of measurements belonging to a given time span and averaging the values of the collected measurements in order to build an average value to be displayed; and
  simultaneously graphically displaying at least three of the measurements of the stored segment on a user interface display.

22. The method as recited in claim 21, further comprising storing the average value in the database.

23. The method as recited in claim 22, further comprising storing the chronological sequence of measurements in the database.

24. A method for processing a chronological sequence of measurements of a time dependent parameter measured in or on a human body comprising:
  storing a time segment of the sequence of measurements as a record in a database;
  generating interpolated values of the time dependent parameter corresponding to intermediate times such that a smooth curve segment is generated; and
  simultaneously graphically displaying at least three of the measurements of the stored segment on a user interface display.

* * * * *

UNITED STATES PATENT AND TRADEMARK OFFICE
CERTIFICATE OF CORRECTION

| | | |
|---|---|---|
| PATENT NO. | : 7,912,674 B2 | Page 1 of 1 |
| APPLICATION NO. | : 12/431904 | |
| DATED | : March 22, 2011 | |
| INVENTOR(S) | : Killoren Clark et al. | |

It is certified that error appears in the above-identified patent and that said Letters Patent is hereby corrected as shown below:

Col. 14, Line 32, "the data collection will may be" should read -- the data collection may be --

Col. 20, Claim 19, Line 21, "household value" should read -- threshold value --

Signed and Sealed this
Sixteenth Day of August, 2011

David J. Kappos
*Director of the United States Patent and Trademark Office*